March 12, 1974 K. K. MESERVE Plant Pat. 3,517
ILEX PLANT (BLUE PRINCE)
Filed Oct. 5, 1972
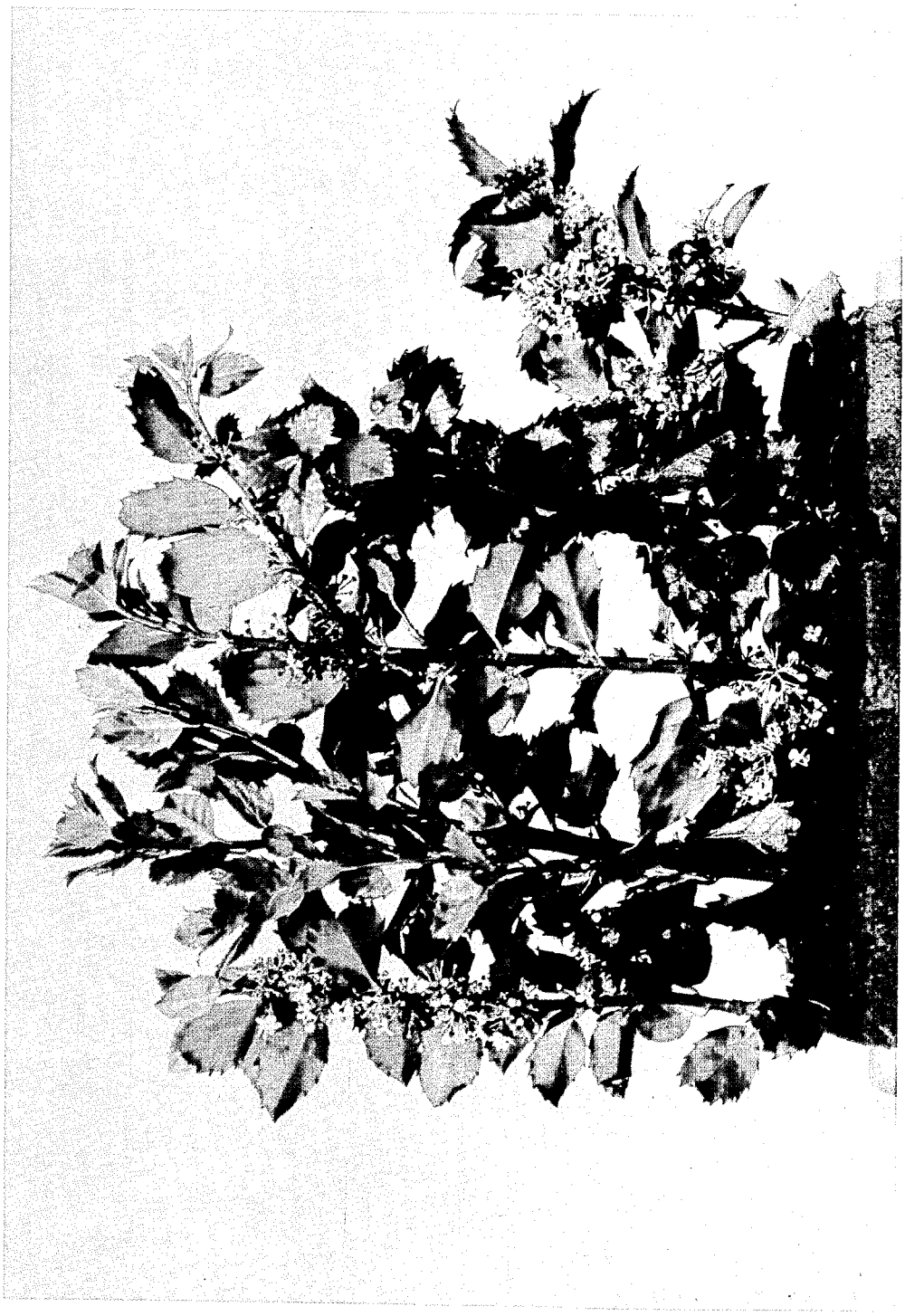

United States Patent Office

Plant Pat. 3,517
Patented Mar. 12, 1974

3,517
ILEX PLANT

Kathleen K. Meserve, St. James, N.Y., assignor to The Conard-Pyle Company, West Grove, Pa.

Filed Oct. 5, 1972, Ser. No. 295,218
Int. Cl. A01h 5/00
U.S. Cl. Plt.—65 1 Claim

ABSTRACT OF THE DISCLOSURE

Ilex produced by crossing an unnamed and unpatented seedling of the species botanically known as *Ilex aquifolium* with another unnamed and unpatented seedling of the species known botanically as *Ilex rugosa.*

SUMMARY OF THE INVENTION

My invention relates to a new, distinctive and useful form of Ilex originated by me by crossing an unnamed and unpatented seedling of the species botanically known as *Ilex aquifolium* with another unnamed and unpatented seedling of the species known botanically as *Ilex rugosa.* These unnamed and unpatented seedlings were my own creations.

The object of my cross was to create a new variety of Ilex with the cold hardiness of *Ilex rugosa* while retaining the pleasing foliage and pleasing manner of growth if *Ilex aquifolium,* which would be useful and attractive in a broad range of landscape applications and over a wider climatic area while serving to enhance the environment. This objective was achieved, along with other improvements, as evidenced by the following unique combination of characteristics which are outstanding in my invention and which distinguish it from its parents and all other varieties of which I am aware:

(1) Bushy, much branched and upright habit of vigorous growth;
(2) Compact, pleasing, natural habit of growth when compared to *Ilex aquifolium;*
(3) An abundance of staminate flowers with pollen produced freely for fertilizing the pistils of many forms of Ilex;
(4) The ability to be sheared and trimmed to be kept within prescribed limits or shaped to a particular space or form;
(5) Deep green foliage with unusual luster to the upper surface;
(6) Mature stems of brown coloration which in combination with the foliage color and luster gives the whole plant a blued-purple color effect;
(7) Longer lived leaves than *Ilex aquifolium* and other hybrids of the same or the reciprocal cross.

Asexual reproduction of my new plant has been accomplished at St. James, N.Y., and at West Grove, Pa. Succeeding propagations have shown the unique combination of characteristics are fully established and transmitted to successive generations.

BRIEF DESCRIPTION OF DRAWING

The accompanying drawing shows typical specimens of my new variety of plant, some with flowers, and as depicted in color as nearly true as is reasonably possible to make the same in a color illustration of this character.

DETAILED DESCRIPTION OF DISCLOSURE

The following is a detailed description of my new variety, with color terminology in accordance with the Royal Horticultural Society Colour Chart of The Royal Horticultural Society, London, England:

Type: Evergreen, single-stemmed shrub.
Class: *Ilex* × *meserveae.*
Parentage; *Ilex aquifolium* seedling × *Ilex rugosa* seedling. Cross made in the spring of 1959; seed sown on Nov. 27, 1959; germination in April 1961; selection made in 1964.
Locality where grown and observed: St. James, N.Y., and West Grove, Pa.
Growth: Upright, center stem, vigorous, bushy, much branched.
Branches: Medium heavy branches occurring freely from the center stem, with succeeding branching developing into a compact, bushy habit of growth.
*Mature branches.*—Brown Group 200A, dull, smooth angled.
*New shoots.*—Yellow-Green Group 146A, somewhat glossy, smooth, angled.
*Branch with flowers.*—Brown Group 200B, dull, smooth, angled.
Foliage: Leaves: simple, alternate, with petioles usually less than ⅕ the length of the leaf and leaves occurring at close intervals on the branches giving dense and full appearance to the plant. Mature leaves 2.5 centimeters to 4.5 centimeters in length, 2.0 centimeters to 3.2 centimeters in width, serrate with 5 to 7 sets of spiny teeth, apex acute and occasionally waxy margins. Texture is firm and stiff.
*Mature leaves in late May.*—Upper surface—Yellow-Green Group 147A, glossy. Lower Surface—Yellow-Green Group 147C, dull.
*New Leaves in late May.*—Upper surface—Yellow-Green Group 144A, very glossy. Lower surface—Yellow-Green Group 146C, satiny.
*Mature leaves in winter.*—Upper surface—Yellow-Green Group 147B, glossy. Lower surface—Yellow-Green Group 147C, dull.
*Young leaves in winter.*—Upper surface—Yellow-Green Group 147A, very glossy. Lower surface—Yellow-Green Group 146B, dull.
Flowers: Staminate flowers are borne in abundant clusters on the preceding year's growth. The flower is carried on a short, stiff, smooth peduncle whose color is Yellow-Green Group 146B.
Bud form is ovoid, smooth with color, Red Group 56D, along margin and color, Red Group 54C, on inner petal area.
Bloom when fully open 5 mm. to 7 mm. in diameter with 4 petals arranged regularly becoming very flat and slightly rolled back before falling clean. Petals are thin, soft and satiny on the outside surface and the inside surface.
*Color.*—Outside surface—Red Group 56D shaded to Red Group 54C. Inside surface—Red Group 56D shaded to Red Group 54C.
Flowers last 1 to 3 days.
*Reproductive organs.*—The staminate flowers have 4 anthers carried on 4 medium-long filaments. Filament color—Red Group 56D. Anther color—Yellow-Green Group 150C.

I claim:

1. A new and distinct variety of evergreen Ilex plant substantially as herein shown and described, characterized particularly as to novelty by a unique combination of vigorous, bushy, much branched, upright habit of growth, producing an unusual quantity of pale pink, staminate flowers which yield an abundance of pollen, and branches of dark color occurring freely and covered with dark green, glossy, stiff foliage, with spiny teeth, combining to give the plant an attractive and pleasing blued-purple color effect, and whose leaves are longer lived than other Ilex of decorative value, and with growth characteristics which are particularly adapted to shearing and trimming to limit or shape the plant, and cold hardiness much greater than its female parent and all other forms of

*Ilex aquifolium,* while retaining the attractive, decorative form of *Ilex aquifolium.*

No references cited.

ROBERT E. BAGWILL, Primary Examiner